United States Patent [19]

Vu'Nguyen

[11] Patent Number: 5,425,752
[45] Date of Patent: Jun. 20, 1995

[54] METHOD OF DIRECT ELECTRICAL MYOSTIMULATION USING ACUPUNCTURE NEEDLES

[76] Inventor: Dung D. Vu'Nguyen, 11, Chaussée de la Muette, Paris, France

[21] Appl. No.: 164,843

[22] Filed: Dec. 9, 1993

Related U.S. Application Data

[63] Continuation of Ser. No. 795,877, Nov. 25, 1991, abandoned.

[51] Int. Cl.⁶ ............................................. A61N 1/00
[52] U.S. Cl. ....................................... 607/72; 607/48; 607/148; 607/76; 128/907
[58] Field of Search .............. 128/907; 607/43, 46, 607/48, 49, 76, 115–117, 148, 149, 150

[56] References Cited

U.S. PATENT DOCUMENTS

| | | | |
|---|---|---|---|
| 3,646,940 | 3/1972 | Timm et al. | 128/784 X |
| 3,897,789 | 8/1975 | Blanchard | 128/422 X |
| 3,908,669 | 9/1975 | Man et al. | 128/422 |
| 3,957,053 | 5/1976 | Woo | 128/907 X |
| 4,026,301 | 5/1977 | Friedman et al. | 128/419 R |
| 4,262,672 | 4/1981 | Kief | 128/422 X |
| 4,326,534 | 4/1982 | Axelgaard | 607/43 |
| 4,342,317 | 8/1982 | Axelgaard | 607/43 |
| 4,392,496 | 7/1983 | Stanton | 128/423 W |
| 4,408,609 | 10/1983 | Axelgaard | 607/43 |
| 4,553,548 | 11/1985 | Varrichio et al. | 607/43 |
| 4,633,888 | 1/1987 | Yoneyama | 128/784 |
| 4,750,499 | 6/1988 | Hoffer | 128/784 |
| 4,799,487 | 1/1989 | Bleicher | 128/419 R |
| 4,932,405 | 7/1990 | Peeters et al. | 128/420.6 X |
| 4,976,264 | 12/1990 | Petrofsky | 607/76 X |
| 5,070,873 | 12/1991 | Graupe et al. | 607/48 |
| 5,133,354 | 7/1992 | Kallok | 607/48 |

OTHER PUBLICATIONS

Meridiens No. 78, pp. 11–21, 1987; Dang-Vu-Nguyen.

Primary Examiner—Lee S. Cohen
Assistant Examiner—Jeffrey R. Jastrzab
Attorney, Agent, or Firm—Hoffman, Wasson & Gitler

[57] ABSTRACT

Direct electrical myostimulation using acupuncture needles as electrodes leads to improvements in the treatment of human muscular ptosis. Pairs of needles are introduced at least as far as the muscular aponeurosis of the ptotic area and a microcurrent is passed between them in line with the muscular fasciculus. The method may advantageously be combined with electrical stimulation of the adipocyte-containing hypoderm to effect lipolysis.

8 Claims, 1 Drawing Sheet

METHOD OF DIRECT ELECTRICAL MYOSTIMULATION USING ACUPUNCTURE NEEDLES

This is a continuation of application Ser. No. 07/795,877 filed on Nov. 25, 1991 now abandoned.

FIELD OF THE INVENTION

This invention relates to a method of direct electrical myostimulation using electrically conducting probes, ideally acupuncture needles, as electrodes.

BACKGROUND OF THE INVENTION

Electrical stimulation of dermal tissue using acupuncture needles as electrodes has already been practised, see Meridiens No. 78 pp 11-21 (1987) by DANG VU NGUYEN incorporated herein by reference.

This reference discloses stimulation of hypodermal adipocytes in order to liberate unwanted deposits of fat (electrolipolysis).

OBJECTS OF THE INVENTION

A primary object of the invention is to provide a method of electrical myostimulation by direct contact with the muscle.

Another object of the invention is a method of treating muscular ptosis in diverse bodily regions, particularly the buttocks, the abdomen, the arms and inner thighs as well as the face and breasts.

A further object is to improve muscle and/or skin tone in any or all of these regions.

SUMMARY OF THE INVENTION

In meeting these and other objects, the present invention provides a method of direct electrical stimulation of a muscle comprising:

introducing at least one pair of electrically conducting probes, preferably acupuncture needles, into a portion of human dermis above the muscle to a depth sufficient to make contact with the muscle; and applying a voltage across the probes so introduced to create a current sufficient to stimulate the muscle.

Although, the present invention has been developed using acupuncture procedures, the inventor is aware that other probes or electrodes than acupuncture needles may be used according to the invention, providing they be of an electrically conducting material which will be in electrical contact with the tissue penetrated.

Thus in what follows, the term "acupuncture needle" may be read as indicating any suitable probe of the kind mentioned above.

DETAILED DESCRIPTION

Figure 1:
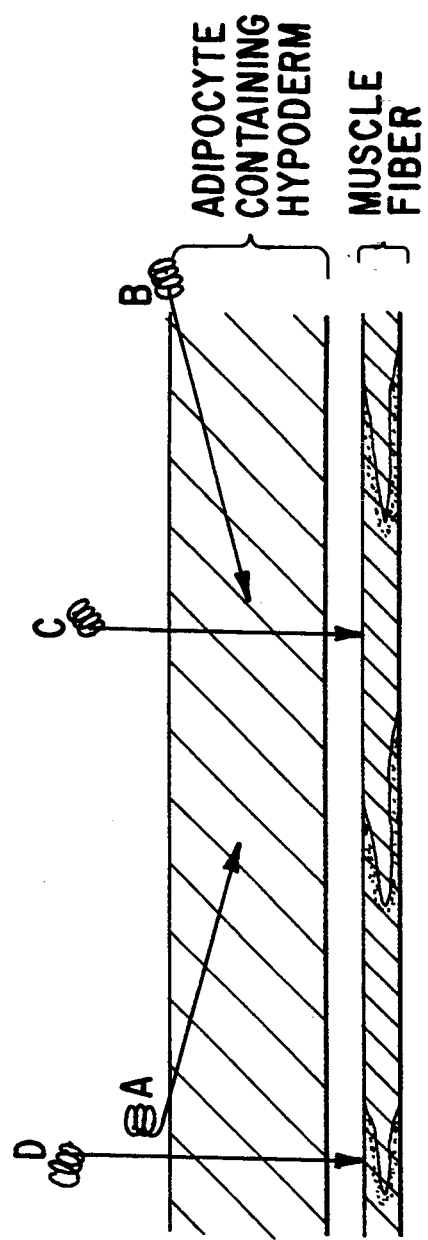
FIG. 1 illustrates a representative insertion method of the probes.

The present invention permits the direct in vivo treatment of muscular ptosis leading to a firming of the muscles and of the overlying skin.

A particular advantage of the direct myostimulation according to the invention is that it appears to reactivate a latent capacity of the CNS to stimulate the treated muscle thus assuring continued stimulation after treatment. This means that once treated, patients may retain the improved muscle tonicity initially established by direct electrostimulation.

The firming of the muscle also leads to a tauter skin and thus to an aesthetic improvement in the treated area.

The method of the invention involves introducing acupuncture needles into the superficial tissues of the human body. This can be done by any skilled acupuncture or medical practitioner.

Needle insertion sites are selected according to the area where treatment is required. If this area includes an acupuncture point or meridien, then insertion at such a point or on such a meridien is preferred. However, the present invention does not rely on needle insertions at such places and is thus not an acupuncture treatment as such.

To contact the muscle according to the invention, the needles must penetrate at least as far as the aponeurosis which is the muscle-tendon forming a broad flat sheet between the muscle and the hypoderm. Preferably, however, they are inserted as far as the first muscular fasciculus or into the muscle mass itself.

Any suitable acupuncture needles may be used according to the invention providing they be of an electrically conducting material. Those supplied by MAISON MEDICAMAT, Malakoff, France or PHU XUAN, Paris, France are particularly suitable.

Generally speaking, the intensity of myostimulation according to the invention (ie the current applied) is lower than for hypodermal lipolysis treatments as the muscle is more sensitive than the fatty hypodermal tissue, the former but not the latter being innervated.

Nevertheless, as the acupuncture needles contacting the muscle also contact the fatty hypodermal layer, it is inevitable, unless very small current intensities are employed, that the method of the invention will achieve a limited degree of incidental lipolysis. In fact, a current as high as can comfortably be stood by the patient is most satisfactory and this will vary with individual patients. Determination of this threshold level requires no special procedure and indeed may be done by the patient himself.

However, in practice, it is preferred to limit the intensity for myostimulation to a range from 2 to 5 $\mu$A and ideally from 2 to 4 $\mu$A.

Thus, the current applied to the muscle according to the invention is preferably below the level at which discomfort might be induced.

This contrasts with the higher intensity of about 8 $\mu$A that may comfortably be applied in "superficial" electrolipolysis (where the acupuncture needles reach only the non-innervated hypodermis).

The figures in microampères ($\mu$A) given in this specification for current are those which give the same mean heating effect as would be obtained with a steady DC of the same value in a pure resistor. For sinusoidal AC, this is the RMS value.

Currents below the stated range will also stimulate the muscle but too little to give good results within an acceptable time frame.

Although it is possible according to the invention to apply direct voltage it is preferable to apply alternating voltage. This may have a variety of waveforms, eg sinusoidal or square wave optionally with preponderantly monopolar cycles to produce, for instance, a pulsing effect.

In this respect, a particularly preferred substantially monopolar waveform is one whose cycle comprises an largely monopolar portion, eg squarewave, followed by very short terminal inversion.

With regard to frequency of this alternating current, it is preferred to begin at low frequency (approximately 10 Hz) and to increase this during treatment to a maximum which may be as high as 50 Hz.

However, for the majority of cases, subjects are preferably treated with a current of frequency between 15 and 25 Hz.

The electrical supply to the electrodes may be any suitable source of electric potential, preferably alternating voltage in the range of 12 to 20 V selected to achieve a current within the range noted above taking account of the distance between pairs of needles and individual skin characteristics.

These parameters can readily be determined by a skilled operative using an ammeter in conjunction with his electrical supply.

Most conveniently, however, the invention may be practised using the STEATRON apparatus sold by MEDICAMAT France which has separate controls for potential, waveform and frequency for up to ten pairs of electrodes.

In the practice of the invention, the number of pairs of needles/electrodes employed can vary over a wide range depending on the condition under treatment but normally 6 to 8 needles are used.

Each pair of needles is placed from 1 to 7 cm, preferably 3 to 5 cm apart, ideally in line with others if more than one pair is to be employed, curvilinearly along the muscle to be treated.

In fact, it is preferred that each pair of needles introduced be in line with the histological direction of muscle fibres of the muscle being stimulated.

In a preferred embodiment, two or more parallel arrays of needles may be used.

It is also preferred that the needles be introduced perpendicularly to the skin although they may be introduced tangentially, as they are for electrolipolysis, or at any intermediate angle.

Conveniently the needles are from 3 to 6 cm long but longer needles may be indicated where the dermis is particularly thick, eg when patients have higher than average deposits of hypodermal fat.

The physician or other skilled operative charged with introducing the needles, being aware of the varying skin thickness of different portions of the human body, knows the approximate depth needed and is able to feel the resistance met when the needle touches the aponeurosis and/or muscle fibres which furthermore will cause the needle to vibrate in sympathy with the natural fibrillation of the muscle.

The patient's own sensations, although not unpleasant, will intensify when the needle reaches the aponeurosis/muscular mass so that his/her verbal indications help to ensure the correct depth of penetration.

When inserted perpendicularly, as is preferred according to the invention, the needles remain upstanding.

On removal, the skin penetrated may be compressed slightly using a cotton swab dipped in alcohol.

The duration of treatment varies in inverse proportion to the intensity and frequency of current used.

Treatment may be carried out for continuous sessions of 20 to 60 minutes, preferably 30 to 50 minutes, repeated weekly for 3 to 6 weeks.

However, best results are achieved when the treatment is applied for approximately 45 minutes and repeated weekly for 4 weeks.

Repeat treatments may advantageously be applied to the same region on the body but with altered needle orientation chosen according to the muscles to be stimulated. The buttocks, for instance, possess a number of axially different muscles so that a particular orientation of needles will favor stimulation of the muscle whose axis corresponds to that orientation.

In a preferred embodiment of the invention, myostimulation is preceded, succeded or accompanied by superficial electrolypolysis (no contact with the muscle) as distinct from the incidental electrolipolysis which might occur during myostimulation.

In FIG. 1, A and B are representative of probes for superficial electrolipolysis and C and D are representative of probes for myostimulation.

According to this preferred embodiment, the needles are firstly introduced only as far as the adipocyte-containing hypoderm where higher current intensities, eg 8 $\mu$A, may be applied for an initial treatment period. Thereafter, either penetration of the existing needles is increased or a fresh set of needles is introduced, in either case as far as the muscle, to practice direct myostimulation at the lower current intensity noted above.

If the same needles are used, it is preferable to reduce or better, switch off, the current before the needles are introduced further.

The above steps may of course be reversed to effect electrolipolysis after direct myostimulation.

Alternatively, the two sets of needles (one for electrolipolysis and one for myostimulation) may be introduced at the same time (preferably tangentially and perpendicularly respectively) for simultaneous treatment.

The following examples are merely for illustration and are not to be taken as limiting the scope of this invention.

EXAMPLES

Example 1

A group of 150 patients suffering from muscular ptosis of the outer thigh were placed on hospital beds for treatment. Three pairs of acupuncture needles of length 4.5 cm were introduced perpendicularly in a linear array into the skin on the outside of both thighs as far as the muscular aponeurosis and in line with the muscle fibres. The distance between each needle was approximately 4 cm and adjacent needles formed a pair. The needles once inserted remained erect and twitched slightly confirming contact with the muscle.

Crocodile clips on individual leads were attached to the end of each needle and the leads connected to three outputs/inputs of a STEATRON by MEDICAMAT.

The controls on the STEATRON were set so as to apply an initial potential between each pair of electrodes of 20 V.

The STEATRON was then switched on and the voltage immediately adjusted to achieve a current in the range 2 to 4 $\mu$A and this level was maintained throughout the treatment. The frequency was adjusted according to the tolerance level of individual patients to lie between 10 and 15 Hz.

Myostimulation was carried out for a total of 50 minutes after which the STEATRON was switched off and the needles slowly removed.

The treatment was repeated with different needle orientation on adjacent parts of the thigh 5 or 6 times on each patient (one session per week).

At the end of the treatment, all patients had developed significant muscle and skin tone in the treated area and the outline of the thigh confirmed a qualitative reversal of femoral ptosis."

Example 2

The same procedure as in example 1 was practiced on a group of 100 patients suffering from a sagging of the musculature around the knee. However, in this case, the patients were allowed to control the level of current themselves by turning the potentiometer knob on the STEATRON. Thus, the highest current sustainable by the patients was applied. This amounted to approximately 3 µA.

The treatment time was 50 minutes using a current of 3 µA at an initial frequency of 15 Hz increased in some cases 50 Hz after 30 minutes.

The treatment was repeated for each patient once a week for 3 weeks.

After treatment, the patients all exhibited firmer soft tissues around the knee with the tissue outline having been considerably improved.

Example 3

A group of 150 patients suffering from muscular ptosis of the trunk and buttocks were treated as follows.

Twelve acupuncture needles of length 10 cm were implanted perpendicularly into the superficial and deep hypoderm as far as the muscular aponeurosis in two parallel lines on the skin's surface in line with the anatomical disposition of the muscle fibres. Then the twelve needles were linked in pairs (adjacent needles in the same line forming a pair) to the electrostimulation apparatus. Stimulation was applied for 50 minutes at a frequency of approximately 15 Hz of variable intensity (2 to 5 µA) according to the level of tolerance of the individual patient.

The total duration of treatment was from 1 to 1.5 months with one session per week.

The treatment was observed to improve the muscle tonicity in the areas affected.

What is claimed is:

1. A method for improving human muscle and skin tone comprising a treatment by myostimulation and superficial electrolipolysis,
   said myostimulation consisting of inserting at least one pair of electrically conducting probes perpendicularly to the muscle, applying an alternating voltage in order to create a current of between 2 and 5 µA, to said at least one pair of electrically conducting probes, said probes being from 1 to 7 cm apart in line with the muscle fibers, and
   said superficial electrolipolysis consisting of inserting at least one pair of electrically conducting probes tangentially in the adipocyte-containing hypoderm, applying a voltage in order to create a current higher than the current used in said myostimulation to said at least one pair of electrically conducting probes,
   said myostimulation and electrolipolysis being carried out simultaneously or one after the other, and
   said treatment being repeated weekly for 3 to 6 weeks.

2. The method of claim 1 wherein said electrically conducting probes are acupuncture needles.

3. The method of claim 1 wherein the alternating voltage used in said myostimulation has a frequency of 10 to 50 Hz.

4. The method of claim 1 wherein the alternating voltage used in said myostimulation has a frequency of 10 to 15 Hz.

5. The method of claim 1 wherein the alternating voltage used in said myostimulation is applied for a duration of 20 to 60 continuous minutes.

6. The method of claim 1 wherein the alternating voltage used in said myostimulation is one whose cycle comprises a monopolar portion followed by a terminal inversion.

7. The method of claim 1 wherein the current used in said superficial electrolipolysis is of 8 µA.

8. The method of claim 1 wherein said treatment further consists of applying said method to a region of the body selected from the group consisting of buttocks, abdomen, arms, thighs, face and breasts.

* * * * *